United States Patent
Hasegawa et al.

(10) Patent No.: US 6,719,887 B2
(45) Date of Patent: Apr. 13, 2004

(54) BIOSENSOR

(75) Inventors: Miwa Hasegawa, Nara (JP); Motokazu Watanabe, Katano (JP); Tomohiro Yamamoto, Hirakata (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 23 days.

(21) Appl. No.: 10/221,990

(22) PCT Filed: Dec. 5, 2001

(86) PCT No.: PCT/JP01/10654

§ 371 (c)(1),
(2), (4) Date: Sep. 17, 2002

(87) PCT Pub. No.: WO02/054054

PCT Pub. Date: Jul. 11, 2002

(65) Prior Publication Data

US 2003/0098234 A1 May 29, 2003

(30) Foreign Application Priority Data

Dec. 27, 2000 (JP) ........................................ 2000-399056

(51) Int. Cl.[7] .............................................. G01N 27/327
(52) U.S. Cl. ............................ 204/403.09; 204/403.06; 204/403.05; 204/418
(58) Field of Search .................. 204/403.05, 403.06, 204/403.07, 403.14, 418, 419, 403.09; 436/70

(56) References Cited

U.S. PATENT DOCUMENTS 4,477,575 A    10/1984   Vogel et al.
5,609,749 A    3/1997    Yamauchi et al.
2003/0183519 A1 * 10/2003 Hasegawa et al. ..... 204/403.14

FOREIGN PATENT DOCUMENTS

| JP | 62-108146 A | * | 5/1987 | .......... G01N/27/30 |
| JP | 63-058149 A |   | 3/1988 | |
| JP | 02-062952 A |   | 3/1990 | |
| JP | 09-318588 A |   | 12/1997 | |

OTHER PUBLICATIONS

JPO abstract of JP 62–108146 A (Kawaguri et al.).*

* cited by examiner

*Primary Examiner*—Alex Noguerola
(74) *Attorney, Agent, or Firm*—Akin Gump Strauss Hauer & Feld, L.L.P.

(57) ABSTRACT

A biosensor includes: an insulating base plate; an electrode system which is provided on the base plate and has a measurement electrode and a counter electrode; a reaction layer including at least oxidoreductase and an electron mediator; a sample solution supply pathway which includes the electrode system and the reaction layer and has an air aperture on the termination side thereof; a sample supply portion; and a filter which is disposed between the sample solution supply pathway and the sample supply portion and filters hemocytes, where plasma with the hemocytes therein filtered with the filter is sucked into the sample solution supply pathway due to capillarity, the central part of a secondary side portion of the filter is protruded into the sample solution supply pathway more than both the right and left ends thereof.

5 Claims, 7 Drawing Sheets

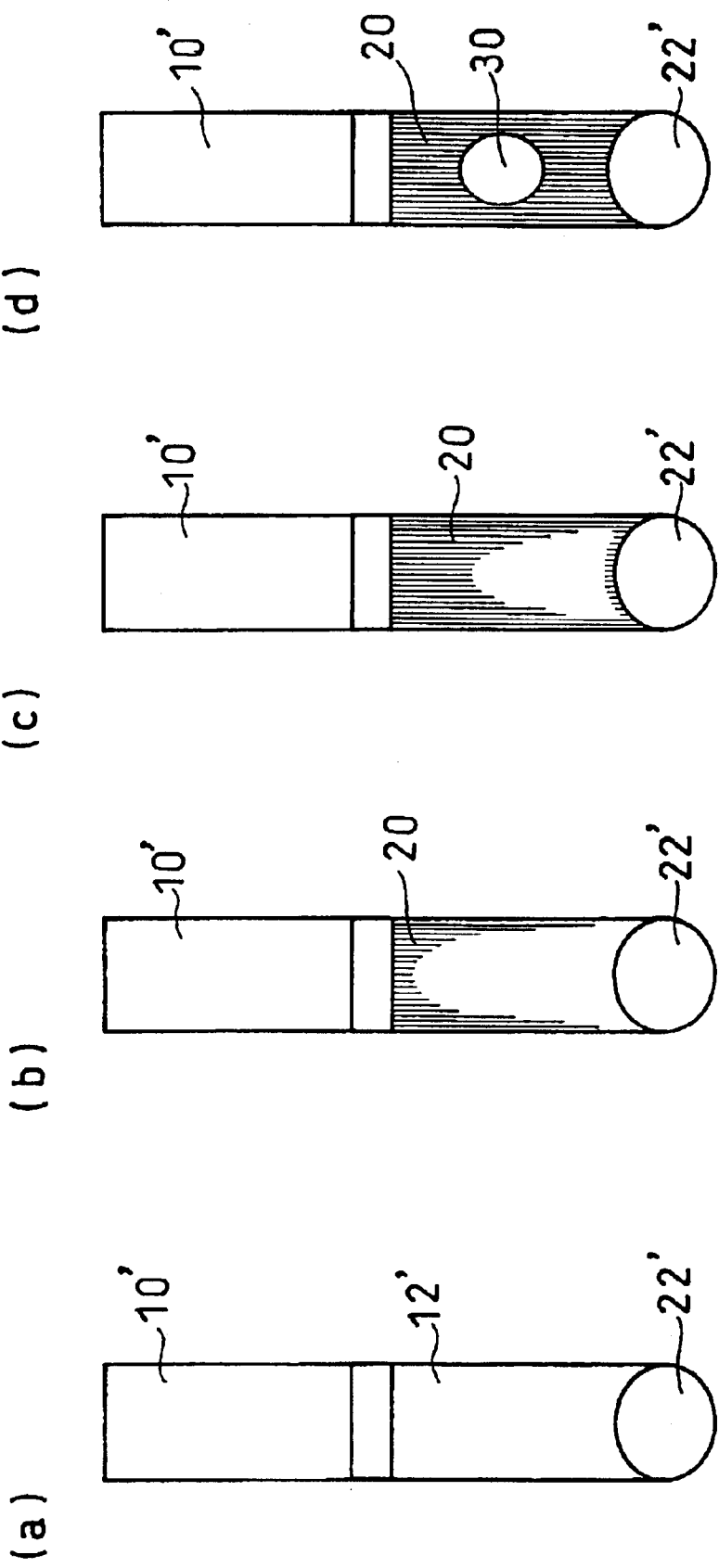

BIOSENSOR

CROSS-REFERENCE TO RELATED APPLICATION

This application is a 371 of International Application No. PCT/JP01/10654, filed Dec. 5, 2001, the disclosure of which is incorporated herein by reference.

TECHNICAL FIELD

The present invention relates to a biosensor, specifically a cholesterol sensor, capable of carrying out speedy, highly-sensitive, simple determination of a specific component in a sample.

BACKGROUND ART

A description will be given to an example of a conventional biosensor, in terms of a glucose sensor.

In a typical glucose sensor, an electrode system including at least a measurement electrode and a counter electrode is formed on an insulating base plate by a method such as screen printing, and an enzyme reaction layer including a hydrophilic polymer, oxidoreductase and an electron mediator is formed on the electrode system. As oxidoreductase used is glucose oxidase; as the electron mediator used is a metal complex, an organic compound or the like, such as potassium ferricyanide, ferrocene derivative or quinone derivative. A buffer is added to the enzyme reaction layer, if necessary.

When a sample solution containing a substrate is dropped onto the enzyme reaction layer in the glucose sensor, the enzyme reaction layer is dissolved to cause a reaction of the enzyme with the substrate. This reaction leads to reduction of the electron mediator. After completion of the enzyme reaction, a substrate concentration in the sample solution can be determined from a value of oxidation current which is generated when this reduced electron mediator is electrochemically oxidized.

Namely, in this type of glucose sensor, a reductant of the electron mediator generated as a result of the enzyme reaction is oxidized on the electrode, to determine a glucose concentration from the oxidation current value.

In theory, such a biosensor is applicable to measurement of diverse substances by using an enzyme whose substrate is an object to be measured. For example, when cholesterol oxidase or cholesterol dehydrogenase and cholesterol esterase are used as oxidoreductase, it is possible to measure a cholesterol value in a serum to be used as a diagnostic indicator in various medical institutions.

Because the enzyme reaction of cholesterol esterase proceeds very slowly, with an appropriate surfactant added thereto, activity of cholesterol esterase can be improved to reduce the time required for the entire reaction.

However, the surfactant included in the reaction system has an adverse effect on hemocytes, making it impossible to measure whole blood itself, as done in the glucose sensor. For this reason, there has been made a proposal that a filter portion is provided in the vicinity of an opening in a sample solution supply pathway for a prompt supply of only plasma with the hemocytes therein filtered, to the sensor.

Nevertheless, a typical enzyme reaction layer includes an easy-to-dissolve part and a hard-to dissolve part. The part along the edge of the sample solution supply pathway is easy to dissolve, whereas the central part thereof is hard to dissolve.

Since the sample solution having passed through the filter flows through the edge of the sample solution supply pathway by priority, it closes an air aperture on the termination side of the sample solution supply pathway before complete dissolution of the central part thereof, leaving bubbles in the central part. In such a case, there is a problem that the sample solution of an amount necessary for measurement is not introduced into the sample solution supply pathway, whereby the enzyme reaction does not proceed sufficiently.

Moreover, there is another problem that the bubbles cover the electrode to reduce the substantial reaction area of the electrode, resulting in a measurement error.

It is thus an object of the present invention to provide a biosensor improved such that plasma with hemocytes therein filtered promptly reaches the electrode system, in order to obviate the disadvantages thus described. Further, it is another object of the present invention to provide a cholesterol sensor with high-accuracy and excellent response, capable of measuring whole blood.

DISCLOSURE OF INVENTION

The present invention relates to a biosensor, comprising: an insulating base plate; an electrode system which is provided on the base plate and has a measurement electrode and a counter electrode; a reaction layer including at least oxidoreductase and an electron mediator; a sample solution supply pathway which includes the electrode system and the reaction layer and has an air aperture on the termination side thereof; a sample supply portion; and a filter which is disposed between the sample solution supply pathway and the sample supply portion and filters hemocytes, where plasma with the hemocytes therein filtered with the filter is sucked into the sample solution supply pathway due to capillarity, and is characterized in that the central part of a secondary side portion of the filter protrudes into the sample solution supply pathway more than both the right and left ends thereof.

It is preferable that the secondary side portion of the filter is arc-shaped or semicircular in the projection thereof drawing to the plane face of the base plate which is the same as the surface thereof.

It is preferable that the sample solution supply pathway has a width of not more than 2.0 mm and the electrode system portion of the sample solution supply pathway has a height of not more than 0.2 mm.

It is also preferable that the biosensor has pressure portions for holding the primary side portion of the filter from the upper and lower sides, and the distance therebetween is not more than 1.5 mm.

It is also preferable that the biosensor has pressure portions for holding the secondary side portion of the filter from the upper and lower sides, and the distance therebetween is not more than 1.5 mm.

It is preferable that the primary side portion of the filter has a width of not more than 5.0 mm.

It is also preferable that the biosensor comprises at the opening in the sample solution supply pathway a concave portion fitted with the upper part or the lower part of the secondary side portion of the filter.

It is also preferable that in the biosensor, the cross sectional area of the sample solution supply pathway is smaller than the cross sectional area of the primary side portion of the filter.

It is also preferable that in the biosensor, the cross sectional area of the secondary side portion of the filter is smaller than the cross sectional area of the primary side portion thereof.

BRIEF DESCRIPTION OF DRAWINGS

FIG. 7 is a diagram explaining the process of flow of plasma into the sample solution supply pathway in a conventional example.

BEST MODE FOR CARRYING OUT THE INVENTION

Figure 1:
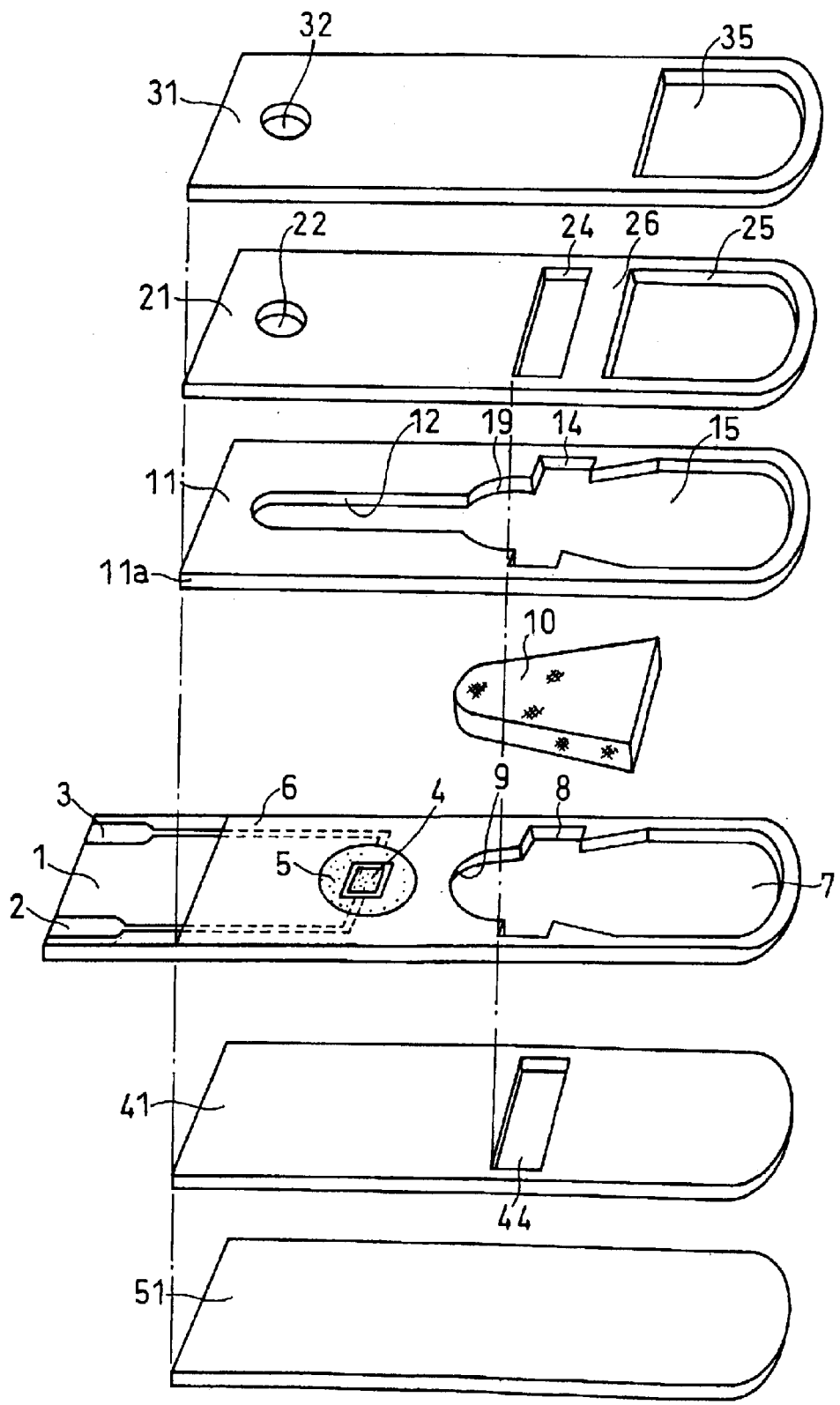
FIG. 1 is an exploded perspective view illustrating a biosensor in accordance with one embodiment of the present invention.

The present invention relates to a biosensor, comprising: an insulating base plate; an electrode system which is provided on the base plate and has a measurement electrode and a counter electrode; a reaction layer including at least oxidoreductase and an electron mediator; a sample solution supply pathway which includes the electrode system and the reaction layer and has an air aperture on the termination side thereof; a sample supply portion; and a filter which is disposed between the sample solution supply pathway and the sample supply portion and filters hemocytes, where plasma with the hemocytes therein filtered with the filter is sucked into the sample solution supply pathway due to capillarity, and is characterized in that the central part of a secondary side portion of the filter protrudes into the sample solution supply pathway more than both the right and left ends thereof.

Herein, the filter to be used in the present invention is composed of a porous material having spaces connecting with one another in a three-dimensional manner. This porous material shifts blood from the sample supply portion side toward the sample solution supply pathway side due to capillarity and functions to filter hemocytes based on a difference in circulation resistances of the plasma and the hemocytes. A non-woven fabric made of a fiber such as glass fiber, cellulose or pulp, filter paper, or another porous material can be applied to the filter. The filter is preferably hydrophilic.

In the biosensor in accordance with the present invention having the structure thus described, the hemocytes, which are interfering substances, are removed with the filter so that the plasma can be promptly flown into the electrode system.

That is to say, because the central part of the secondary side portion of the filter protrudes into the sample solution supply pathway more than both the right and left ends of the secondary portion, the plasma flows into the central part of the sample solution supply pathway by priority. Since this plasma completely dissolves reagent layers such as a reaction layer and a hydrophilic polymer layer disposed in the central part of the sample solution supply pathway, the filtered plasma can be promptly flown into the sample solution supply pathway without leaving bubbles in the central part.

Normally, the reaction layer is formed by developing and drying an aqueous solution of the reagent. Affected by the fact that the central part of such a reaction layer becomes thicker than the end thereof, the sample solution (plasma) flows into the thinner part (end) of the reaction layer in the sample solution supply pathway, to fill in the air aperture before complete dissolution of the central part of the reaction layer.

As opposed to this, according to the present invention, protrusion of the central part of the secondary side portion of the filter into the sample solution supply pathway permits the priority flow of the sample solution into the central part of the sample solution supply pathway.

It is to be noted that: the primary side portion of the filter refers to a portion including the point which firstly gets in contact with and then absorbs the sample solution upon the dropping thereof onto the biosensor; the secondary side portion of the filter refers to a portion including the point out of which the sample solution (plasma) goes out toward the inside of the sample solution supply pathway.

The electron mediator for use in the present invention can be selected from potassium ferricyanide, a redox compound having the electron transferring ability to and from oxidoreductase such as cholesterol oxidase, or the like.

Oxidoreductase is an enzyme whose substrate is an object to be measured. Glucose oxidase is applied to a sensor where glucose is the object to be measured. For measurement of a cholesterol value in blood serum to be used as a diagnostic indicator, enzyme cholesterol oxidase for catalyzing an oxidation reaction of cholesterol, or enzyme cholesterol esterase for catalyzing the process of changing cholesterol dehydrogenase and cholesterol ester to cholesterol, is used. Because the enzyme reaction of cholesterol esterase proceeds very slowly, with an appropriate surfactant added thereto, activity of cholesterol esterase can be improved to reduce the time required for the entire reaction.

The electron mediator and oxidoreductase are disposed on or in the vicinity of the electrode system in the sensor. In a sensor which is combined with the base plate provided with the electrode system and comprises a cover member, which forms the sample solution supply pathway for a supply of the sample solution to the electrode system between the base plate and the sensor, the electron mediator and oxidoreductase can be arranged in the place such as the portion exposed to the sample solution supply pathway or the opening in the sample solution supply pathway.

Wherever the place is, it is preferable that the sample solution introduced can dissolve the reaction layer with ease and then arrive at the electrode system. It is also preferable to form the hydrophilic polymer layer in contact with the upper face of the electrode system so as to protect the electrode and prevent the reaction layer formed from being peeled off. Instead of forming the hydrophilic polymer layer on the electrode system, it may be formed as the base of the reaction layer, or the hydrophilic polymer may be included in the bottom reaction layer.

The reaction layer including the electron mediator is preferably separated from the surfactant for enhancing the solubility thereof. Also, the reaction layer including the electron mediator is preferably separated from enzyme cholesterol esterase, which catalyzes the oxidation reaction of cholesterol, for the sake of preservation stability.

There has been made a proposal that in a biosensor for measuring a blood sugar level, a layer containing lipid is formed so as to cover a layer formed on the electrode system, or the like, to facilitate introduction of the sample solution to the reaction layer (Japanese Laid-Open Patent Publication No. 2-062952, for example). In the biosensor for measuring cholesterol in accordance with the present invention, it is preferable to form a part of the reaction layer by freeze-drying or to fix the surfactant on the cover member itself. Application of such a structure eliminates the need for formation of a lipid layer.

The example of the hydrophilic polymer includes water-soluble cellulose derivatives such as ethyl cellulose, hydroxypropyl cellulose or carboxymethyl cellulose, polyvinyl pyrrolidone, polyvinyl alcohol, gelatin, polyacrylic acid and the salts thereof, starch and the derivatives thereof, polymers of maleic anhydride or the salts thereof, polyacrylamide, methacrylate resin, and poly-2-hydroxyethyl methacrylate.

The surfactant can be selected from among n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis (3-D-gluconeamidopropyl) deoxycholeamide and polyoxyethylene (10) octyl phenyl ether.

When lipid is used, an amphipathic phospholipid such as lecithin, phosphatidyl choline or phosphatidyl ethanolamine can be preferably used.

As the measuring method of the oxidation current, a two-electrode system composed only of a measurement electrode and a counter electrode and a three-electrode system further comprising a reference electrode are applicable, and in the three-electrode system, more accurate measurement is possible.

In the following, the present invention will be described in detail with the use of concrete embodiments, referring to drawings.

FIG. 1 is an exploded perspective view illustrating a biosensor in accordance with a preferred embodiment.

An insulating base plate 1 is made of an insulating resin such as polyethylene terephthalate. On the upper face of the left side of the base plate 1 in FIG. 1, a silver paste is printed by screen printing to form leads 2 and 3, and the base of an electrode system. A conductive carbon paste including a resin binder is further printed on the base plate 1 to form an electrode system including a measurement electrode 4 and a counter electrode 5.

An insulating paste is also printed in a specific region to form an insulating layer 6. The insulating layer 6 keeps the exposed areas of the measurement electrode 4 and the counter electrode 5 constant and partly covers the leads 2 and 3.

The base plate 1 further comprises an opening 7 on the right side portion thereof. A semicircular portion 9 on the electrode system side of the opening 7 has the form of a substantially semicircle in a projection thereof drawing to the flat face which is the same as the surface of the base plate, so as to locate the end of the secondary side portion of the below-mentioned filter 10. A square concave portion 8 is provided adjacently to the semicircular portion 9.

A spacer 11 to be combined with the base plate 1 comprises a slit 12 for forming the below-mentioned sample solution supply pathway on the left and an opening 15 on the right, which is shaped identically to the opening 7 in the base plate 1. The opening 15 comprises a semicircular portion 19 on the left and a square concave portion 14 adjacently thereto.

An upper auxiliary cover 21 comprises: an air aperture 22 communicating to the termination side of the slit 12 in the spacer 11; an opening 25 communicating to the right-half of the opening 15 in the spacer 11 and to the right-half of the opening 7 in the base plate 1; and opening 24 communicating to the concave portions 14 and 8 of the openings 15 and 7, respectively; and a partition portion 26 for partitioning the openings 24 and 25. An upper cover 31 comprises an air aperture 32 and an opening 35 communicating, respectively, to the air aperture 22 and the opening 25 in the upper auxiliary cover 21.

A lower auxiliary cover 41 comprises an opening 44 in correspondence with the opening 24 in the upper auxiliary cover 21. A lower auxiliary cover 51 is made of a flat plate.

The above-mentioned upper cover 31, upper auxiliary cover 21, spacer 11, lower auxiliary cover 41 and lower cover 51 are made of polyethylene terephthalate, as in the case with the base plate 1.

The filter 10 is made of glass-fiber filter paper, and in the projection thereof drawing to the plane face which is the same as the base plate 1, it comprises a trapezoid portion 10a with an upper hem of 2 mm, a lower hem of 4 mm and a height of 5 mm, and a semicircular portion 10b with a radius of 1 mm connecting with the upper hem of the trapezoid portion 10a.

Figure 2:
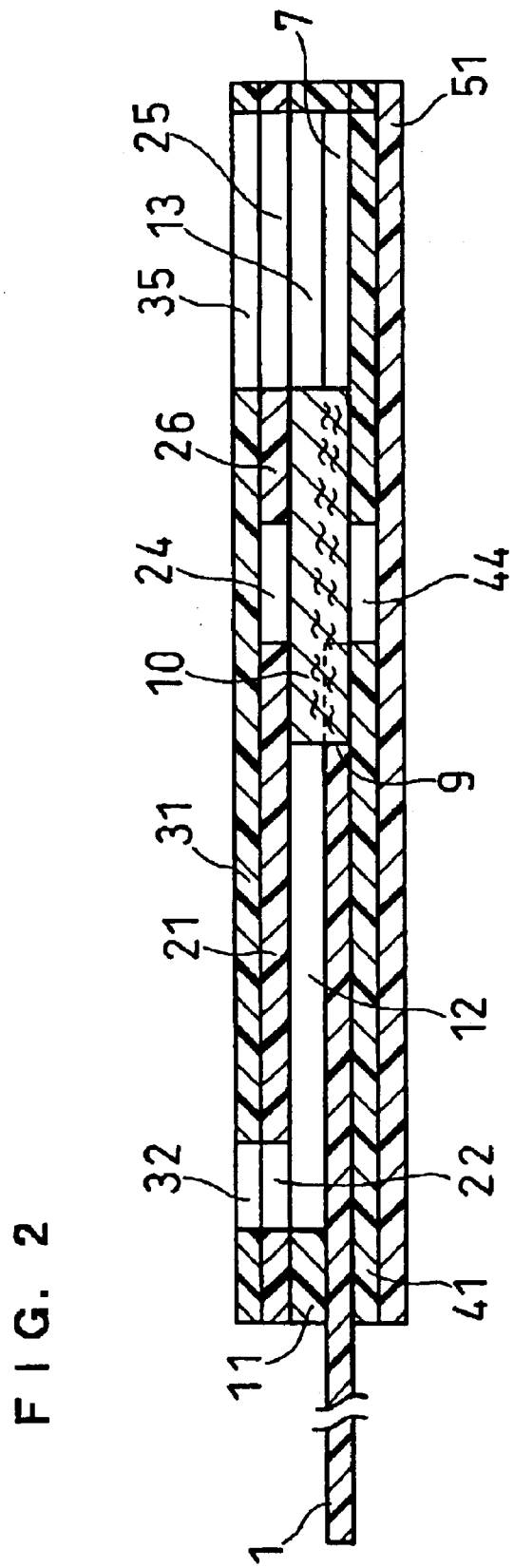
FIG. 2 is a longitudinal sectional view illustrating the biosensor of FIG. 1.

This sensor is fabricated by forming a reaction layer on a predetermined member as described below, placing the lower auxiliary cover 41 on the lower cover 51 and placing the base plate 1 on the lower auxiliary cover 41 such that the left edge of the insulting layer 6 of the base plate 1 are aligned with the left edge of the lower auxiliary cover 41. The filter 10 is then set on the lower auxiliary cover 41 such that the secondary side portion, namely the left edge, of the filter 10 is fit in the semicircular portion 9 of the base plate 1 and the semicircular portion 19 of the spacer 11. On these members, subsequently, the spacer 11, the upper auxiliary cover 21 and the upper cover 31 are combined. Herewith, lamination of the base plate 1, the spacer 11, the auxiliary covers 21 and 41, and the covers 31 and 51 in such a positional relation shown by the dashed line in FIG. 1 enables fabrication of such a sensor as shown in FIG. 2.

In the filter 10, the partition portion 26 of the upper auxiliary cover 21 and the lower cover 41 press the lower hem side, namely the primary side portion, of the trapezoid portion 10a from the upper and lower sides. The upper auxiliary cover 21 and the lower auxiliary cover 41 also press the termination of the secondary side portion from the upper and lower sides. The opening 35 in the upper cover 31, the opening 25 in the upper auxiliary cover 21, the right side portion of the opening 15 in the spacer 11 and the right side portion of the opening 7 in the base plate 1 are communicated, to form a concave portion whose bottom is the lower auxiliary cover 41. This concave portion serves as a sample supply portion.

The opening 24 in the upper auxiliary cover 21, the opening 44 in the lower auxiliary cover 41, and the concave portions 14 and 8 of the openings 15 and 7, which correspond to the opening 24 and the opening 44, form a space surrounding the filter 10. As this space being present, it is possible to prevent hemocytes from flowing through the surfaces of the upper auxiliary cover 21, the lower auxiliary cover 41 and the like, which are holding the filter, into the electrode system, instead of passing through the filter.

Figure 3:
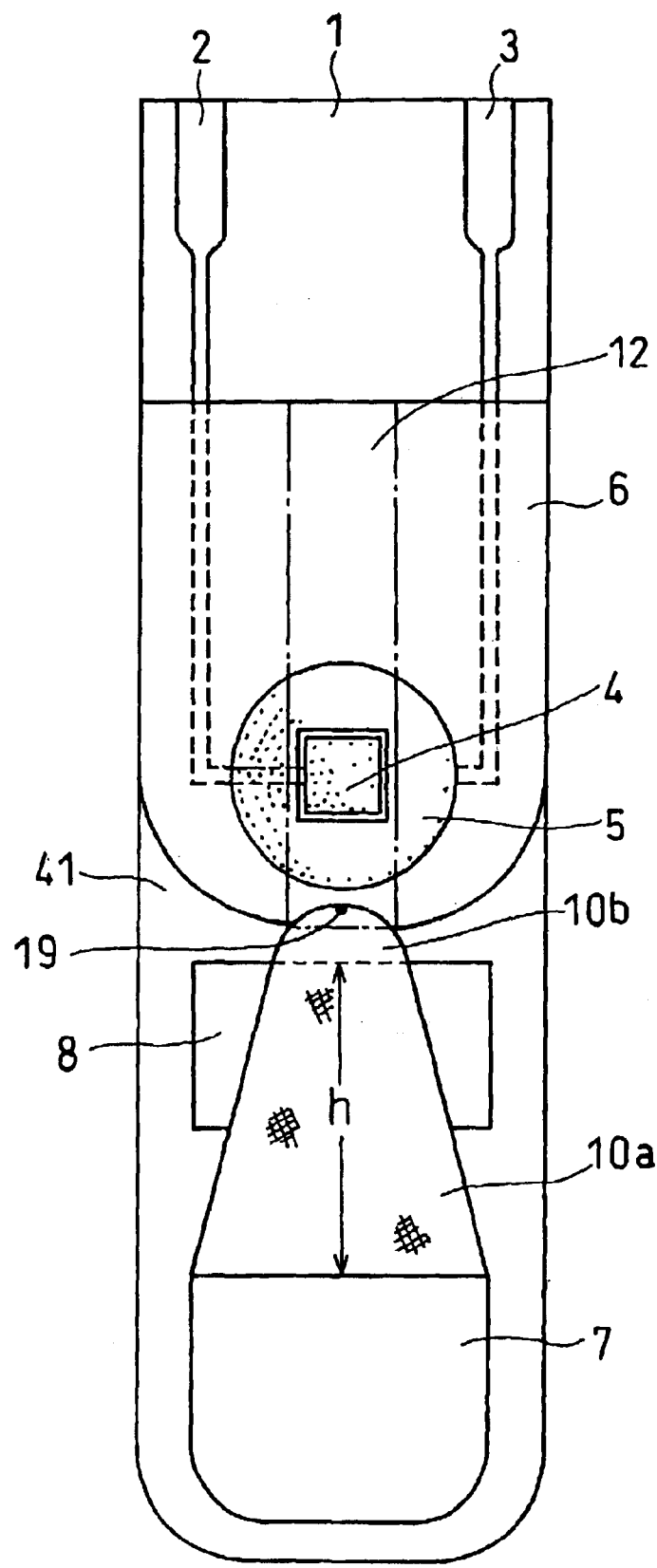
FIG. 3 is a plane view illustrating the biosensor of FIGS. 1 and 2, with the exceptions of the reaction layer and the upper cover member.

The space formed by the slit 12 in the spacer 11 between the base plate 1 and the upper auxiliary cover 21 forms a sample solution supply pathway. The termination of this sample solution supply pathway communicates to the outside through the air apertures 22 and 32. The end of the secondary side of the filter 10 is involved in the leader of the sample solution supply pathway. The cross-section of the sample solution supply pathway is rectangular, whose shorter side corresponds to the direction of height of the sample solution supply pathway. As evidenced by FIG. 2, the leader of the sample solution supply pathway has a depth equivalent to the thickness of the base plate in the semicircular portion 9 of the base plate 1. The leader of the secondary side portion of the filter 10 having been involved in this part is semicircular in the projection thereof drawing to the plane face which is the same as the surface of the base plate 1, and the central part protrudes into the sample solution supply pathway, as can be seen from FIG. 3.

The example of the filter whose leader of the secondary side portion is semicircular in the projection thereof drawing to the plane face which is the same as the surface of the base plate 1 may include a triangular or home base-shaped filter in the projection thereof drawing to the plane face which is the same as the surface of the base plate 1.

Figure 4:
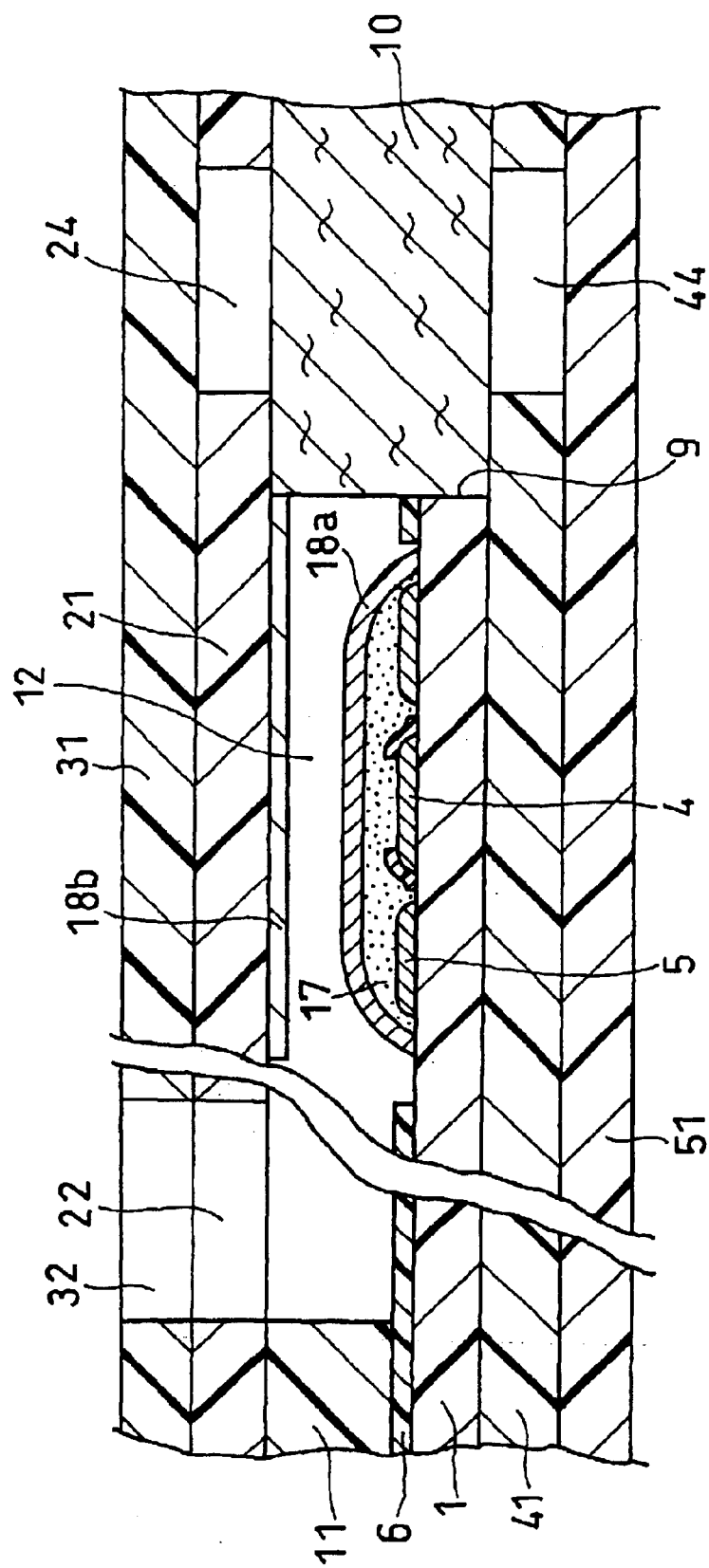
FIG. 4 is an enlarged sectional view illustrating the substantial part of the biosensor of FIGS. 1 to 3.

A reaction layer is omitted from FIG. 2, whereas it is shown in FIG. 4. A hydrophilic polymer layer 17 and a reaction layer 18a are formed on the electrode system of the base plate 1. A reaction layer 18b is formed on the lower face side of the upper auxiliary cover 21, which equates to the ceiling of the sample solution supply pathway. The spacer 11 is bonded to the upper auxiliary cover 21, the whole is turned upside down to form the concave portion with the slit 12, and a solution for forming a reaction layer is dropped onto the obtained concave portion, followed by drying, to form the reaction layer 18b.

While the biosensor shown in FIG. 1 is produced using six types of members so as to make the configuration thereof easy to understand, the upper cover 31 and the upper auxiliary cover 21, or further including the spacer 11, may be composed of one member. The lower auxiliary cover 41 and the under cover 51, or further including the base plate 1, can also be composed of one member.

For measurement of cholesterol in blood with the use of this sensor, blood as a sample is supplied from the opening 35 in the upper cover 31 to the concave portion serving as a sample supply portion. The blood supplied here infiltrates from the termination of the primary side portion of the filter 10 thereinto. In the filter 10, plasma exudes from the termination of the secondary side portion of the filter because the infiltrating rate of hemocytes is slower than that of the plasma which is a liquid component. The exuded plasma then fills the entire sample solution supply pathway from the vicinity of the electrode system to the air aperture 22 while dissolving a reaction reagent carried on the position covering the electrode system or the reverse face of the cover immediately above the electrode system.

Once the entire sample solution supply pathway is filled with the liquid, the flow of the liquid within the filter 10 also stops and hence the hemocytes are hold in the position at that time, without arriving at the termination of the secondary side portion of the filter 10. Accordingly, the filter 10 is designed to have a difference in flow resistances to the plasma and the hemocytes to the extent that, when the plasma of enough an amount to fill the entire sample solution supply pathway passes through the filter, the hemocytes have not reached the secondary side portion of the filter. A depthfilter having a pore size of about 1 to 7 $\mu$m is favorably applied to the filter of the present invention.

After undergoing the process of filtering the hemocytes as thus described, a chemical reaction of the reaction layer dissolved by the plasma with a component to be measured (cholesterol in the case of a cholesterol sensor) in the plasma occurs, and a current value in the electrode reaction is measured after a lapse of predetermined time to determine the component in the plasma.

FIG. 4 represents an example of disposition of the reaction layer in the vicinity of the electrode system of the sample solution supply pathway. On the electrode system of the base plate 1 formed are the layer 17 of sodium carboxymethyl cellulose as the hydrophilic polymer and the layer 18a including the reaction reagent e.g. the electron mediator. On the reverse face of the cover member given by combining the upper cover 31, the upper auxiliary cover 21 and the spacer 11, the reaction layer 18b including oxidoreductase is formed on the surface exposed to the sample solution supply pathway.

As represented in FIGS. 1 to 4, any of the cross sectional area of the slit 12 constituting the sample solution supply pathway, which is vertical to the direction of the flowing liquid, is made smaller than the cross sectional area of the filter 10. The filter 10 is constituted so as to have substantially uniform density on the whole. By making the cross sectional area of the sample solution supply pathway smaller than the cross sectional area of the primary side portion of the filter 10 as thus described, the plasma with the hemocytes therein filtered with the filter can be promptly sucked into the sample solution supply pathway due to capillarity.

As described above, the reaction layer generally comprises an easy-to-dissolve part and a hard-to-dissolve part. The edge of the sample solution supply pathway, namely the portion along the wall face of the slit 12 in the spacer 11, is easy to dissolve, whereas the central part of the sample solution supply pathway is hard to dissolve. Since the sample solution having passed through the filter flows along the spacer by priority, there may be cases where the sample solution fills in the air aperture before complete dissolution of the central part. Protrusion of the central part of the secondary side portion of the filter into the sample solution supply pathway more than the both right and left ends thereof enables the priority flow of the sample solution through the central part of the sample solution supply pathway, whereby the plasma can be promptly flown into the sensor without leaving bubbles on the central part of the sample solution supply pathway.

Figure 5:
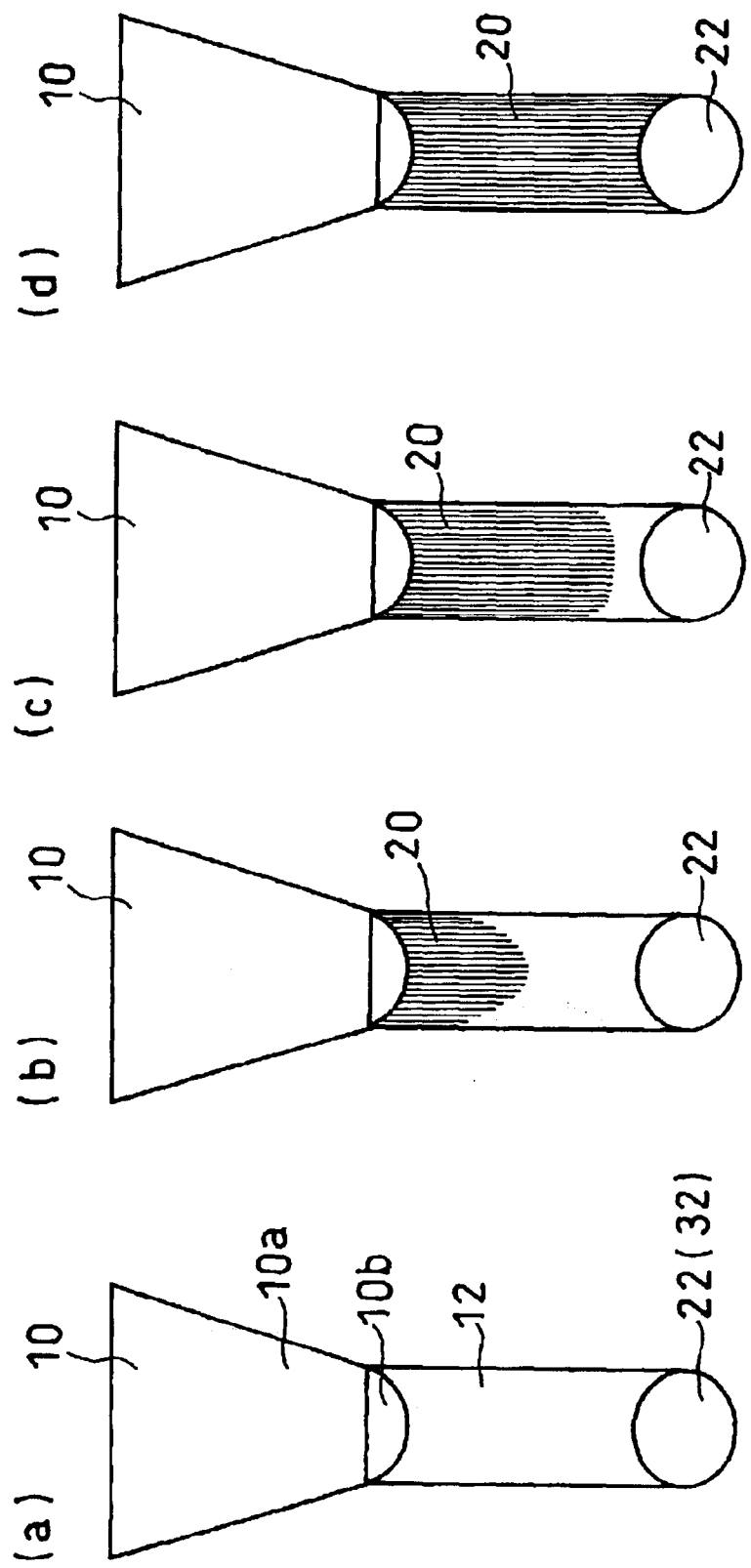
FIG. 5 is a diagram explaining the process of flow of plasma into the sample solution supply pathway.

FIG. 5 is a diagram explaining the process of flow of the filtered plasma into the sample solution supply pathway, which shows a plane view representing the sample solution supply pathway 12, the air aperture 22(32) and the filter 10. A reference alphabet (a) indicates an initial state while a reference alphabet (b) indicates a state in which the plasma 20 having been filtered with the filter 10 begins to enter the sample solution supply pathway 12. As can be seen from (b), protrusion of the central part of the secondary side portion of the filter protrudes into the sample solution supply pathway more than the both right and left ends thereof allows the priority flow of the plasma 20 through the central part of the sample solution supply pathway. Since the plasma thus arrives at the air aperture 22, the sample solution supply pathway will not be in the state with the bubbles included.

On the other hand, FIG. 7 represents the flow of the plasma in the case of using a conventional filter 10' whose end is plane. Since a reagent layer of the portion along the edge of a sample solution supply pathway 12' is easy to dissolve, plasma flows through the end of the sample solution supply pathway by priority, and the state is therefore likely to be formed that the sample solution supply pathway includes the bubbles 30 in the central part thereof.

In the biosensor constituted as illustrated, the primary side portion of the filter preferably has a width of not more than 5 mm and a thickness of not more than 1 mm. The opening in the sample solution supply pathway preferably has a width of not more than 2 mm and a height of not more than 200 μm. When the filter has a thickness of 450 μm and the sample solution supply pathway has a height of 100 μm, for example, the base plate preferably has a thickness of about 350 μm.

Below, an example of the present invention will be described.

EXAMPLE 1

In the present example, a cholesterol sensor having the structures of FIGS. 1 to 4, where the reaction layer 18a included the electron mediator and the reaction layer 18b included cholesterol oxidase, cholesterol esterase and the surfactant, was produced.

First, 5 μl of an aqueous solution containing 0.8% by weight sodium carboxymethyl cellulose (hereinafter simply referred to as CMC) was dropped onto the electrode system of the base plate 1, and dried in a drying apparatus with warm blast of 50° C. for 10 minutes to form the CMC layer 17 as the hydrophilic polymer layer.

Next, 4 μl of potassium ferricyanide aqueous solution (corresponding to 70 mA of potassium ferricyanide) was dropped onto the CMC layer 17, and dried in the drying apparatus with warm blast of 50° C. for 10 minutes to form the layer 18a including potassium ferricyanide.

Polyoxyethylene(10)octyl phenyl ether (TritonX-100) as a surfactant was added to an aqueous solution prepared by dissolving cholesterol oxidase originating from Nocardia (EC1.1.3.6) and cholesterol esterase originating from Pseudomonas (EC.3.1.1.13) in water. 1.3 μl of the obtained mixed solution was dropped onto the concave portion formed on the slit 12 in the cover member, which was obtained by combining the upper cover 31, the upper auxiliary cover 21 and the spacer 11, frozen with liquid nitrogen of −196° C., and dried in a flask set in a freeze-drying apparatus overnight, to form the reaction layer 18b including 1 unit (U)/sensor of cholesterol oxidase, 2.5 U/sensor of cholesterol esterase, and 2% by weight of the surfactant.

The spacer 11 used here had a thickness of 100 mm, and the electrode system portion of the sample solution supply pathway had a height of 100 mm. The opening in this sample solution supply pathway was a portion corresponding to the semicircular portion 9 of the opening 7 in the base plate 1, having a depth equivalent to the thickness of the base plate 1 of 350 mm. The sample solution supply pathway had a width of 2 mm.

The filter 10 was produced using a glass fiber filter having a thickness of about 450 μm. This filter was punched out to be a shape comprised of the trapezoid portion 10a with an upper hem of 2 mm, a lower hem of 4 mm and a height of 5 mm, and the semicircular portion 10b with a radius of 1 mm connecting with the upper hem of the trapezoid portion 10a. The obtained filter 10 was disposed such that the end thereof was fit in the concave portion 7 of the base plate.

Subsequently, the cover member comprising the above-mentioned three members was bonded to the member prepared by integrating the base plate 1, the lower auxiliary cover 41 and the lower cover 51, to produce a cholesterol sensor.

20 μl of whole blood as the sample solution were introduced into the sample supply portion of this sensor through the opening 35 and, three minutes after the introduction, a pulse voltage of +0.5 V was applied toward the anode on the measuring electrode relative to the counter electrode and, five seconds after the application, the value of the current flowing between the working electrode and the counter electrode was measured. The results are shown in FIG. 6 and Table 1.

TABLE 1

| Total cholesterol concentration (mg/dl) | 0 | 85 | 155 | 295 |
| --- | --- | --- | --- | --- |
| Average response value (μA) | 0.7 | 1.4 | 2.5 | 4.4 |
| Variation coefficient (%) | 3.0 | 5.3 | 5.9 | 4.5 |

Figure 6:
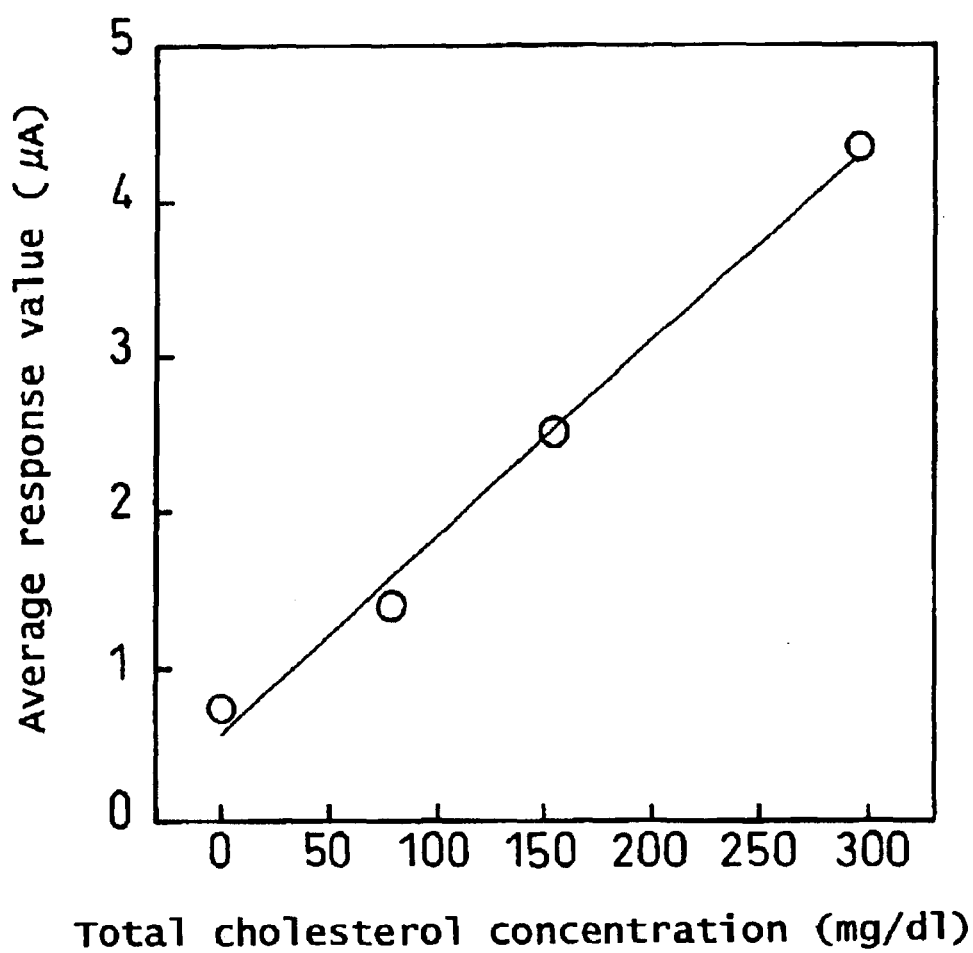
FIG. 6 is a diagram showing a response characteristic of the cholesterol sensor in the example of the present invention.

As is evident from FIG. 6, according to the sensor in accordance with the present invention, a favorable linearity between the cholesterol concentration and the response value can be obtained.

INDUSTRIAL APPLICABILITY

According to the biosensor in accordance with the present invention, hemocytes, which are interfering substances, can be removed with a filter, without generating bubbles, and even in a case where the bubbles are generated, they can be easily removed, allowing a prompt supply of plasma with the hemocytes therein removed to the electrode system. The present invention can therefore provide an electrochemical biosensor with an excellent response characteristic.

What is claimed is:

1. A biosensor, comprising: an insulating base plate having a planar face; an electrode system which is provided on said base plate and has a measurement electrode and a counter electrode; a reaction layer including at least oxidoreductase and an electron mediator; a sample solution supply pathway which includes an opening said electrode system and said reaction layer, and has an air aperture on the termination side thereof; a sample supply portion; and a filter which is disposed between said sample solution supply pathway and said sample supply portion and filters hemocytes, where plasma with hemocytes therein filtered with said filter is sucked into said sample solution supply pathway due to capillarity, characterized in that the central part of a secondary side portion of said filter protrudes into said sample solution supply pathway more than both the right and left ends thereof.

2. The biosensor in accordance with claim 1, characterized in that said secondary side portion of said filter is arc-shaped or semicircular in the projection thereof onto the plane face of said base plate.

3. The biosensor in accordance with claim 1, characterized in that said sample solution supply pathway comprises at the opening therein a concave portion fitted with the upper part or the lower part of said secondary side portion of said filter.

4. The biosensor in accordance with claim 1, characterized in that the cross sectional area of said sample solution supply pathway is smaller than the cross sectional area of a primary side portion of said filter.

5. The biosensor in accordance with claim 1, characterized in that the cross sectional area of said secondary side portion of said filter is smaller than the cross sectional area of said primary side portion thereof.

* * * * *

UNITED STATES PATENT AND TRADEMARK OFFICE
CERTIFICATE OF CORRECTION

PATENT NO. : 6,719,887 B2
DATED : April 13, 2004
INVENTOR(S) : Miwa Hasegawa et al.

It is certified that error appears in the above-identified patent and that said Letters Patent is hereby corrected as shown below:

Column 10,
Line 37, please insert a comma after the word "opening" so the line should read:
-- supply pathway which includes an opening, said electrode --

Signed and Sealed this

Sixteenth Day of November, 2004

JON W. DUDAS
Director of the United States Patent and Trademark Office